(12) United States Patent
Xie et al.

(10) Patent No.: US 9,663,379 B2
(45) Date of Patent: May 30, 2017

(54) METHOD FOR PREPARING ZEOLITE SSZ-98

(71) Applicant: Chevron U.S.A. Inc., San Ramon, CA (US)

(72) Inventors: Dan Xie, Richmond, CA (US); Christopher Michael Lew, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 140 days.

(21) Appl. No.: 14/865,631

(22) Filed: Sep. 25, 2015

(65) Prior Publication Data

US 2017/0088432 A1    Mar. 30, 2017

(51) Int. Cl.
*C01B 39/30* (2006.01)
*B01J 29/50* (2006.01)
*C07C 1/20* (2006.01)

(52) U.S. Cl.
CPC ............ *C01B 39/305* (2013.01); *B01J 29/50* (2013.01); *C07C 1/20* (2013.01); *C07C 2529/50* (2013.01)

(58) Field of Classification Search
CPC .......... C01B 39/305; B01J 29/50; C07C 1/20; C07C 2529/50
See application file for complete search history.

(56) References Cited

U.S. PATENT DOCUMENTS

| | | |
|---|---|---|
| 4,840,780 A | 6/1989 | Valyocsik |
| 9,409,786 B2 | 8/2016 | Xie et al. |
| 9,416,017 B2 | 8/2016 | Xie et al. |
| 2006/0073094 A1 | 4/2006 | Miller et al. |
| 2013/0059723 A1 | 3/2013 | Yilmaz et al. |
| 2016/0001273 A1 | 1/2016 | Xie et al. |
| 2016/0264428 A1* | 9/2016 | Moulton ................ C01B 39/48 |

OTHER PUBLICATIONS

International Search Report, International Appl. No. PCT/US2016/051443, mailed Dec. 16, 2016.

* cited by examiner

*Primary Examiner* — David M Brunsman
(74) *Attorney, Agent, or Firm* — Terrence M. Flaherty

(57) ABSTRACT

A method is disclosed for preparing zeolite SSZ-98 using N,N-dimethylpiperidinium cations as a structure directing agent.

10 Claims, 2 Drawing Sheets

METHOD FOR PREPARING ZEOLITE SSZ-98

TECHNICAL FIELD

This disclosure relates generally to a method for preparing zeolite SSZ-98 using N,N-dimethylpiperidinium cations as a structure directing agent.

BACKGROUND

Molecular sieves are a commercially important class of crystalline materials. They have distinct crystal structures with ordered pore structures which are demonstrated by distinct X-ray diffraction patterns. The crystal structure defines cavities and pores which are characteristic of the different species.

Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three letter code and are described in the "*Atlas of Zeolite Framework Types,*" Sixth Revised Edition, Elsevier (2007).

ERI framework type materials are characterized by three-dimensional 8-membered-ring pore/channel systems containing double-six-rings (d6r) and cages. Small pore zeolites containing d6r building units and cages have shown utility in methanol-to-olefins catalysis and in the selective catalytic reduction of nitrogen oxides ($NO_x$) to name some of the more important commercial applications.

U.S. patent application Ser. Nos. 14/323,444 and 14/323,473 disclose an ERI framework type molecular sieve designated SSZ-98 and its synthesis using N,N'-dimethyl-1,4-diazabicyclo[2.2.2]octane dications as a structure directing agent.

It has now been found that N,N-dimethylpiperidinium cations are effective as a structure directing agent in the synthesis of SSZ-98.

SUMMARY

In one aspect, there is provided a method of preparing zeolite SSZ-98 by contacting under crystallization conditions (1) at least one source of silicon oxide; (2) at least one source of aluminum oxide; (3) at least one source of potassium; (4) N,N-dimethylpiperidinium cations; and (5) hydroxide ions.

In another aspect, there is provided a process for preparing zeolite SSZ-98 by: (a) preparing a reaction mixture containing: (1) at least one source of silicon oxide; (2) at least one source of aluminum oxide; (3) at least one source of potassium; (4) N,N-dimethylpiperidinium cations; (5) hydroxide ions; and (6) water; and (b) subjecting the reaction mixture to crystallization conditions sufficient to form crystals of the zeolite.

In one aspect, there is provided zeolite SSZ-98 containing N,N-dimethylpiperidinium cations within its pore structure.

In another aspect, there is also provided crystalline zeolite SSZ-98 having a composition, as-synthesized and in the anhydrous state, in terms of mole ratios, as follows:

|  | Broad | Exemplary |
|---|---|---|
| $SiO_2/Al_2O_3$ | 10 to 50 | 15 to 35 |
| $Q/SiO_2$ | 0.02 to 0.20 | 0.05 to 0.20 |
| $K/SiO_2$ | 0.01 to 0.20 | 0.02 to 0.15 | wherein Q represents N,N-dimethylpiperidinium cations.

DETAILED DESCRIPTION

Figure 1:
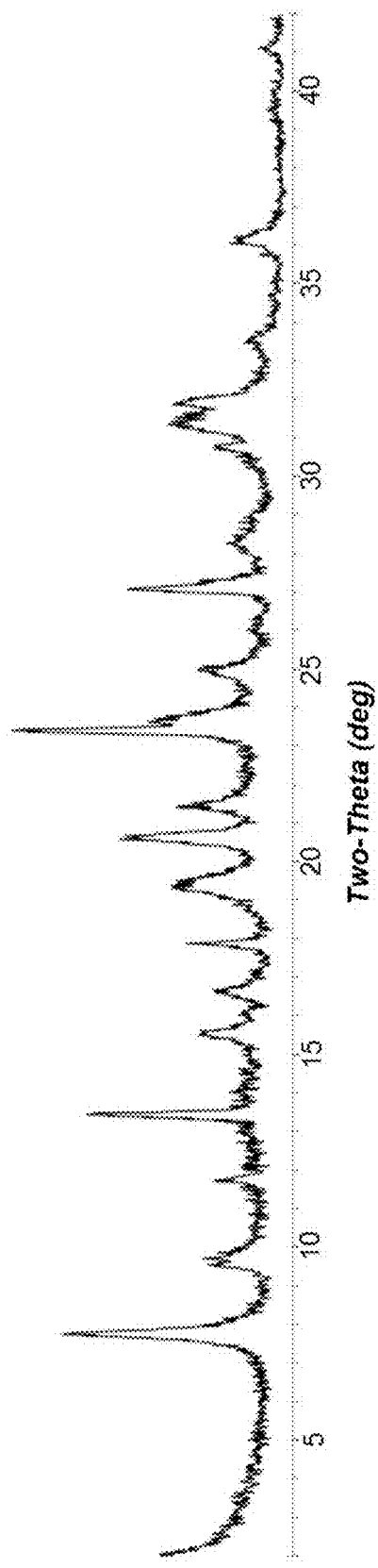
FIG. 1 is a powder X-ray diffraction pattern (XRD) of the as-synthesized zeolite prepared in Example 1.

The following terms will be used throughout the specification and will have the following meanings unless otherwise indicated.

The term "zeolite" refers to crystalline aluminosilicate compositions which are microporous and which are formed from corner-sharing $AlO_2$ and $SiO_2$ tetrahedra.

As used herein, the numbering scheme for the Periodic Table Groups is as disclosed in *Chem. Eng. News,* 63(5), 26-27 (1985).

In preparing zeolite SSZ-98, an N,N-dimethypiperidinium cation is used as a structure directing agent ("SDA"), also known as a crystallization template. The SDA useful for making SSZ-98 is represented by the following structure (1):

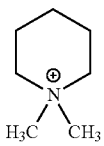

(1)

N,N-dimethylpiperidinium cation

The SDA cation is associated with anions which can be any anion that is not detrimental to the formation of the zeolite. Representative anions include elements from Group 17 of the Periodic Table (e.g., fluoride, chloride, bromide, and iodide), hydroxide, sulfate, tetrafluoroborate, acetate, carbon/late, and the like.

Reaction Mixture

In general, zeolite SSZ-98 is prepared by: (a) preparing a reaction mixture containing (1) at least one source of silicon oxide; (2) at least one source of aluminum oxide; (3) at least one source of potassium; (4) N,N-dimethylpiperidinium cations; (5) hydroxide ions; and (6) water; and (b) subjecting the reaction mixture to crystallization conditions sufficient to form crystals of the zeolite.

The composition of the reaction mixture from which the zeolite is formed, in terms of mole ratios, is identified in Table 1 below:

TABLE 1

|  | Broad | Exemplary |
|---|---|---|
| $SiO_2/Al_2O_3$ | 10 to 100 | 15 to 80 |
| $K/SiO_2$ | 0.05 to 0.45 | 0.15 to 0.40 |
| $Q/SiO_2$ | 0.10 to 0.80 | 0.15 to 0.30 |
| $OH/SiO_2$ | 0.20 to 1.00 | 0.20 to 0.60 |
| $H_2O/SiO_2$ | 10 to 50 | 15 to 35 | wherein compositional variable Q represents N,N-dimethylpiperidinum cations.

Sources useful herein for silicon oxide include fumed silica, precipitated silicates, silica hydrogel, silicic acid, colloidal silica, tetra-alkyl orthosilicates (e.g., tetraethyl orthosilicate), and silica hydroxides.

Sources useful herein for aluminum oxide include aluminates, alumina, and aluminum compounds (e.g., aluminum chloride, aluminum hydroxide, and aluminum sulfate), kaolin clays, and other zeolites (e.g., zeolite Y).

Suitable sources of potassium include any potassium salt which is not detrimental to the crystallization of the zeolite, though potassium hydroxide is typically used.

Optionally, the reaction mixture may contain seed crystals. In one embodiment, synthesis of the crystalline zeolite is facilitated by the presence of 0.05 to 10.0 wt. % (e.g., from 1 to 5 wt. %) seed crystals based on the total weight of the reaction mixture. The seed crystals can be isostructural with the desired zeolite, for example, the product of a previous synthesis.

For each embodiment described herein, the reaction mixture can be supplied by more than one source. Also, two or more reaction components can be provided by one source.

The reaction mixture can be prepared either batch wise or continuously. Crystal size, morphology and crystallization time of the crystalline zeolite described herein can vary with the nature of the reaction mixture and the crystallization conditions.

Crystallization and Post-Synthesis Treatment

Crystallization of the zeolite can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 1 day to 14 days.

Once the zeolite crystals have formed, the solid product is separated from the reaction mixture by standard mechanical separation techniques such as centrifugation or filtration. The crystals are water-washed and then dried to obtain the as-synthesized zeolite crystals. The drying step is typically performed at a temperature of less than 200° C.

As a result of the crystallization process, the recovered crystalline zeolite product contains within its pore structure at least a portion of the structure directing agent used in the synthesis.

The structure directing agent is typically at least partially removed from the zeolite by calcination before use. Calcination consists essentially of heating the zeolite comprising the structure directing agent at a temperature of from 200° C. to 800° C. in the presence of an oxygen-containing gas, optionally in the presence of steam. The structure directing agent can also be removed by photolysis techniques as described in U.S. Pat. No. 6,960,327.

To the extent desired and depending on the composition of the zeolite, any cations in the as-synthesized or calcined zeolite can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the term "as-synthesized" refers to the zeolite in its form after crystallization, prior to removal of the SDA cation.

The zeolite disclosed herein can be formulated with into a catalyst composition by combination with other materials, such as binders and/or matrix materials, which provide additional hardness or catalytic activity to the finished catalyst.

Characterization of the Zeolite

SSZ-98 zeolites made by the process disclosed herein have a composition (in terms of mole ratios), as-synthesized and in the anhydrous state, as described in Table 2 below:

TABLE 2

|  | Broad | Exemplary |
|---|---|---|
| $SiO_2/Al_2O_3$ | 10 to 50 | 15 to 35 |
| $Q/SiO_2$ | 0.02 to 0.20 | 0.05 to 0.20 |
| $K/SiO_2$ | 0.01 to 0.20 | 0.02 to 0.15 | wherein compositional variable Q represents N,N-dimethylpiperidinium cations.

It should be noted that the as-synthesized form of the SSZ-98 zeolite may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

SSZ-98 is characterized by an X-ray diffraction pattern which, in the as-synthesized form of the zeolite, includes at least the lines set out in Table 3 below.

TABLE 3

Characteristic Peaks for As-Synthesized SSZ-98

| 2-Theta[a] | d-spacing (nm) | Relative Intensity[b] |
|---|---|---|
| 7.78 | 1.136 | VS |
| 9.74 | 0.907 | W |
| 11.79 | 0.750 | W |
| 13.46 | 0.657 | S |
| 14.10 | 0.627 | W |
| 15.53 | 0.570 | M |
| 16.62 | 0.533 | W |
| 19.51 | 0.455 | W |
| 20.56 | 0.432 | VS |
| 21.40 | 0.415 | M |
| 23.38 | 0.380 | S |
| 23.76 | 0.374 | VS |
| 24.88 | 0.358 | W |

[a] ±0.20
[b] The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

In its calcined form, the aluminosilicate SSZ-98 zeolite disclosed herein has a composition comprising the molar relationship:

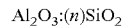

$Al_2O_3:(n)SiO_2$ wherein n has a value of from 10 to 50 (e.g., from 10 to 35, from 15 to 50, or from 15 to 35).

SSZ-98 is characterized by an X-ray diffraction pattern which, in the calcined form of the zeolite, includes at least the lines set out in Table 4.

TABLE 4

Characteristic Peaks for Calcined SSZ-98

| 2-Theta[a] | d-spacing (nm) | Relative Intensity[b] |
|---|---|---|
| 7.76 | 1.138 | VS |
| 9.78 | 0.904 | W |
| 11.79 | 0.750 | W |
| 13.45 | 0.658 | VS |
| 14.07 | 0.629 | W |
| 15.51 | 0.571 | W |
| 16.61 | 0.533 | W |

TABLE 4-continued

Characteristic Peaks for Calcined SSZ-98

| 2-Theta[a] | d-spacing (nm) | Relative Intensity[b] |
|---|---|---|
| 19.50 | 0.455 | W |
| 20.54 | 0.432 | S |
| 21.39 | 0.415 | W |
| 23.37 | 0.380 | M |
| 23.73 | 0.375 | S |
| 24.92 | 0.357 | W |

[a]±0.20
[b]The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern. Notwithstanding these minor pertubations, the basic crystal structure remains unchanged.

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks, and d, the interplanar spacing corresponding to the recorded lines, can be calculated.

In one embodiment, zeolite SSZ-98 prepared in accordance with this disclosure is preferably substantially free of non-ERI framework type material. By "substantially free of non-ERI framework type material" is meant that the zeolite composition disclosed herein contains less than 2.5% non-ERI framework type character (e.g., less than 1% non-ERI framework type character, less than 0.5% non-ERI framework type character, or no measurable non-ERI framework type character), as measured by X-ray diffraction. The presence of these impurities can be determined and quantified by analysis of the X-ray diffraction pattern of a sample. The term "non-ERI framework type material" used herein means any material that does not contain crystalline zeolite of the ERI framework type. Examples of such non-ERI framework type material include, for example, amorphous material and OFF framework type zeolites.

EXAMPLES

The following illustrative examples are intended to be non-limiting.

Example 1

0.88 g of 45% KOH solution, 5.40 g of deionized water and 1.00 g of CBV720 Y zeolite (Zeolyst International, $SiO_2/Al_2O_3$ mole ratio=30) were mixed together in a Teflon liner. Then, 4.46 g of 11.15% N,N-dimethylpiperidinium hydroxide solution was added to the mixture. The resulting gel was stirred until it became homogeneous. The liner was capped and placed within a Parr steel autoclave reactor. The autoclave was placed in an oven and heated at 150° C. for 3 days. The solid products were recovered from the cooled reactor by centrifugation, washed with deionized water and dried at 95° C.

Figure 2:
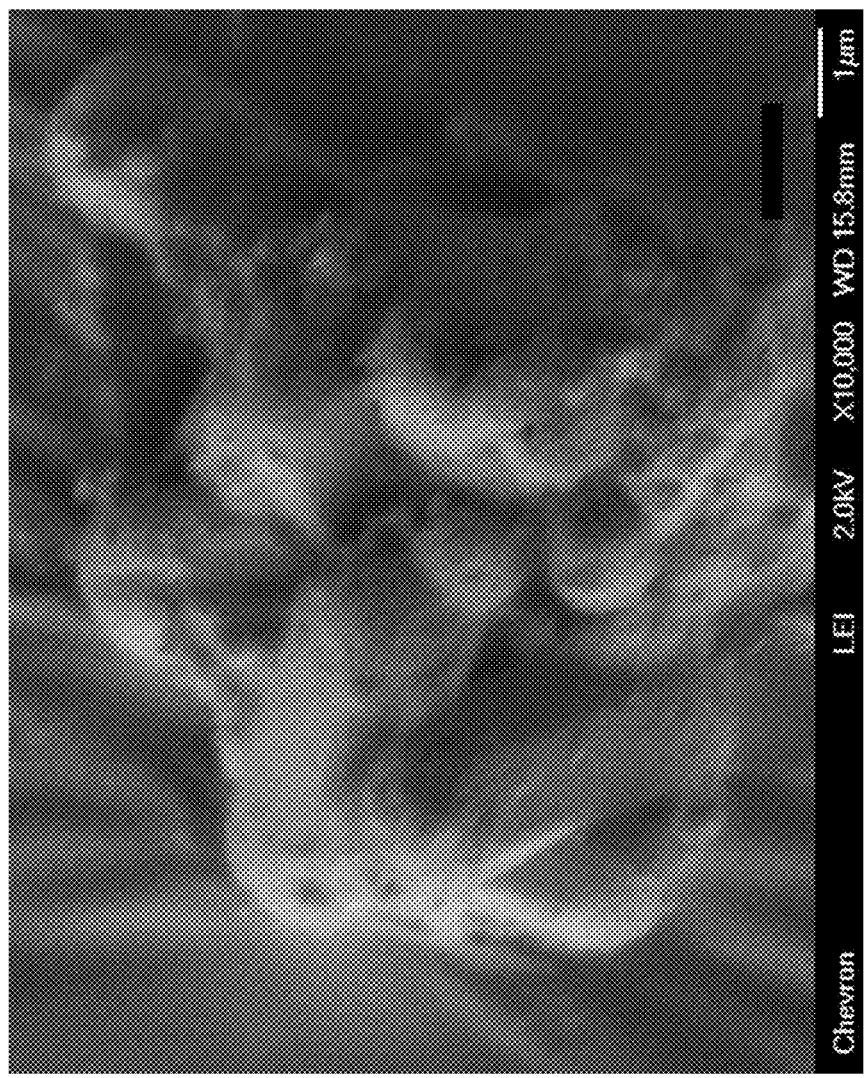
FIG. 2 is a scanning electron micrograph (SEM) image of the as-synthesized zeolite prepared in Example 1.

The resulting product was analyzed by powder XRD and SEM. The powder XRD pattern is shown in FIG. 1 and indicates that the material is pure SSZ-98 zeolite. The SEM image is shown in FIG. 2 and indicates a uniform field of crystals.

The product had a $SiO_2/Al_2O_3$ mole ratio of 12.6, as determined by ICP elemental analysis.

Example 2

1.81 g of 45% KOH solution, 11.14 g of deionized water and 2.00 g of CBV760 Y-zeolite (Zeolyst International, $SiO_2/Al_2O_3$ mole ratio=60) were mixed together in a Teflon liner. Then, 9.20 g of 11.15% N,N-dimethylpiperidinium hydroxide solution was added to the mixture. The resulting gel was stirred until it became homogeneous. The liner was capped and placed within a Parr steel autoclave reactor. The autoclave was placed in an oven and heated at 150° C. for 3 days. The solid products were recovered from the cooled reactor by centrifugation, washed with deionized water and dried at 95° C.

The resulting product was identified by powder XRD and SEM to be pure SSZ-98 zeolite.

The product had a $SiO_2/Al_2O_3$ mole ratio of 14.7, as determined by ICP elemental analysis.

Example 3

0.91 g of 45% KOH solution, 5.62 g of deionized water and 1.00 g of CBV780 Y-zeolite (Zeolyst International, $SiO_2/Al_2O_3$ mole ratio=80) were mixed together in a Teflon liner. Then, 4.64 g of 11.15% N,N-dimethylpiperidinium hydroxide solution was added to the mixture. The resulting gel was stirred until it became homogeneous. The liner was capped and placed within a Parr steel autoclave reactor. The autoclave was placed in an oven and heated at 150° C. for 3 days. The solid products were recovered from the cooled reactor by centrifugation, washed with deionized water and dried at 95° C.

The resulting product was identified by powder XRD and SEM to be pure SSZ-98 zeolite.

The product had a $SiO_2/Al_2O_3$ mole ratio of 16.2, as determined by ICP elemental analysis.

Example 4

1.82 g of 45% KOH solution, 13.29 deionized water, 2.00 g of CBV780 Y-zeolite (Zeolyst International, $SiO_2/Al_2O_3$ mole ratio=80) and 0.20 g of SSZ-98 seeds obtained from a previous synthesis were mixed together in a Teflon liner. Then, 6.96 g of 11.15% N,N-dimethylpiperidinium hydroxide solution was added to the mixture. The resulting gel was stirred until it became homogenous. The liner was then capped and placed within a Parr steel autoclave reactor. The autoclave was then put in an oven and heated at 150° C. for 2 days. The solid products were recovered from the cooled reactor by centrifugation, washed with deionized water and dried at 95° C.

The resulting zeolite product was identified by powder XRD and SEM as a pure SSZ-98 zeolite.

The product had a $SiO_2/Al_2O_3$ mole ratio of 16.8, as determined by ICP elemental analysis.

Example 5

The as-synthesized zeolite product of Example 1 was calcined inside a muffle furnace under a flow of air heated to 540° C. at a rate of 1° C./minute and held at 540° C. for 5 hours, cooled and then analyzed by powder XRD. The powder XRD pattern indicated that the material remains stable after calcination to remove the organic SDA.

Example 6

The calcined product from Example 5 (K-SSZ-98) was treated with 10 mL (per g of zeolite) of a 1N ammonium nitrate solution at 90° C. for 2 hours. The solution was cooled, decanted off and same process repeated.

The product ($NH_4$-SSZ-98) after drying was subjected to a micropore volume analysis using $N_2$ as adsorbate and via the BET method. The zeolite exhibited a micropore volume of 0.25 $cm^3/g$.

Example 7

Methanol Conversion

Ammonium-exchanged SSZ-98 from Example 6 was pelletized at 5 kpsi, crushed and meshed to 20-40. 0.20 g of catalyst (diluted 4:1 v/v with alundum) was centered in a stainless steel downflow reactor in a split tube furnace. The catalyst was pre-heated in-situ under flowing nitrogen at 400° C. A feed of 10% methanol in nitrogen was introduced into the reactor at a rate of 1.3 $h^{-1}$ WHSV.

Reaction data was collected using a plug flow and an Agilent on-line gas chromatograph with an FID detector. Reaction products were analyzed at various times on an HP-PLOT Q column. The results are summarized in Table 5.

TABLE 5

| Product | 0.4 Hour Data | 1.5 Hour Data | 2.6 Hour Data | 3.3 Hour Data |
|---|---|---|---|---|
| Conversion | 1.00 | 1.00 | 1.00 | 1.00 |
| Sum $C_1$-$C_3$ paraffins | 0.18 | 0.14 | 0.11 | 0.15 |
| Ethylene | 0.46 | 0.54 | 0.72 | 0.61 |
| Propylene | 0.24 | 0.23 | 0.14 | 0.11 |
| Summed Butanes/Butenes | 0.11 | 0.08 | 0.01 | 0.02 |
| Summed Pentanes/Pentenes | 0.02 | 0.02 | 0.03 | 0.11 |
| Ethylene/Propylene ratio | 1.91 | 2.37 | 5.30 | 5.72 |

The products shown in Table 5 are consistent with those for a small pore zeolite in terms of product shape-selectivity in the reaction of methanol being catalytically converted to olefins of mostly $C_2$-$C_4$ size. No aromatic products were observed.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. A method of preparing zeolite SSZ-98, comprising:
   (a) preparing a reaction mixture containing:
      (1) at least one source of silicon oxide;
      (2) at least one source of aluminum oxide;
      (3) at least one source of potassium;
      (4) N,N-dimethylpiperidinium cations (Q);
      (5) hydroxide ions; and
      (6) water; and
   (b) subjecting the reaction mixture to crystallization condition sufficient to form crystals of the zeolite.

2. The method of claim 1, wherein the zeolite is prepared from a reaction mixture comprising, in terms of mole ratios, the following:

| | |
|---|---|
| $SiO_2/Al_2O_3$ | 10 to 100 |
| $K/SiO_2$ | 0.05 to 0.45 |
| $Q/SiO_2$ | 0.10 to 0.80 |
| $OH/SiO_2$ | 0.20 to 1.00 |
| $H_2O/SiO_2$ | 10 to 50. |

3. The method of claim 1, wherein the zeolite is prepared from a reaction comprising, in terms of mole ratios, the following:

| | |
|---|---|
| $SiO_2/Al_2O_3$ | 15 to 80 |
| $K/SiO_2$ | 0.15 to 0.40 |
| $Q/SiO_2$ | 0.15 to 0.30 |
| $OH/SiO_2$ | 0.20 to 0.60 |
| $H_2O/SiO_2$ | 15 to 35. |

4. The method of claim 1, wherein the zeolite has a composition, as-synthesized and in the anhydrous state, in terms of mole ratios, as follows:

| | |
|---|---|
| $SiO_2/Al_2O_3$ | 10 to 50 |
| $Q/SiO_2$ | 0.02 to 0.20 |
| $K/SiO_2$ | 0.01 to 0.20. |

5. The method of claim 1, wherein the zeolite has a composition, as-synthesized and in the anhydrous state, in terms of mole ratios, as follows:

| | |
|---|---|
| $SiO_2/Al_2O_3$ | 15 to 35 |
| $Q/SiO_2$ | 0.05 to 0.20 |
| $K/SiO_2$ | 0.02 to 0.15. |

6. The method of claim 1, wherein the zeolite has, in its as-synthesized form, an X-ray diffraction pattern including the following lines:

| 2-Theta | d-spacing (nm) | Relative Intensity |
|---|---|---|
| 7.78 ± 0.20 | 1.136 | VS |
| 9.74 ± 0.20 | 0.907 | W |
| 11.79 ± 0.20 | 0.750 | W |
| 13.46 ± 0.20 | 0.657 | S |
| 14.10 ± 0.20 | 0.627 | W |
| 15.53 ± 0.20 | 0.570 | M |
| 16.62 ± 0.20 | 0.533 | W |
| 19.51 ± 0.20 | 0.455 | W |
| 20.56 ± 0.20 | 0.432 | VS |
| 21.40 ± 0.20 | 0.415 | M |
| 23.38 ± 0.20 | 0.380 | S |
| 23.76 ± 0.20 | 0.374 | VS |
| 24.88 ± 0.20 | 0.358 | W. |

7. An SSZ-98 zeolite comprising N,N-dimethylpiperidinium cations within in its pore structure.

8. The zeolite of claim 7, wherein the zeolite has a $SiO_2/Al_2O_3$ mole ratio of from 10 to 50.

9. The zeolite of claim 7, wherein the zeolite has a $SiO_2/Al_2O_3$ mole ratio of from 15 to 35.

10. The zeolite of claim 7, having, in its as-synthesized form, an X-ray diffraction pattern including the following lines:

| 2-Theta | d-spacing (nm) | Relative Intensity |
|---|---|---|
| 7.78 ± 0.20 | 1.136 | VS |
| 9.74 ± 0.20 | 0.907 | W |
| 11.79 ± 0.20 | 0.750 | W |
| 13.46 ± 0.20 | 0.657 | S |
| 14.10 ± 0.20 | 0.627 | W |
| 15.53 ± 0.20 | 0.570 | M |
| 16.62 ± 0.20 | 0.533 | W |
| 19.51 ± 0.20 | 0.455 | W |
| 20.56 ± 0.20 | 0.432 | VS |
| 21.40 ± 0.20 | 0.415 | M |
| 23.38 ± 0.20 | 0.380 | S |
| 23.76 ± 0.20 | 0.374 | VS |
| 24.88 ± 0.20 | 0.358 | W. |

\* \* \* \* \*